US00PP11329P

United States Patent [19]

Leis et al.

[11] Patent Number: Plant 11,329

[45] Date of Patent: Apr. 4, 2000

[54] STRAWBERRY PLANT NAMED 'TETHIS'

[75] Inventors: Michelangelo Leis; Dario Musacchi; Alessio Martinelli, all of Ferrara, Italy

[73] Assignee: C.I.V. Consorzio Italiano Vivaisti, Ferrara, Italy

[21] Appl. No.: 09/103,713

[22] Filed: Jun. 23, 1998

[51] Int. Cl.[7] ..... A01H 5/00

[52] U.S. Cl. ..... Plt./208

[58] Field of Search ..... Plt./208

[56] References Cited

U.S. PATENT DOCUMENTS

P.P. 8,535 1/1994 Musacchi et al. ..... Plt./208
P.P. 10,780 2/1999 Ackerman et al. ..... Plt./208

*Primary Examiner*—Howard J. Locker
*Assistant Examiner*—Wendy A Baker
*Attorney, Agent, or Firm*—Christie, Parker & Hale, LLP

[57] ABSTRACT

A new strawberry plant providing large, firm fruit of bi-conical shape.

4 Drawing Sheets

BACKGROUND OF THE INVENTION

The new variety of strawberry was created in a breeding program by crossing as male parent the variety 'Chandler' (U.S. Plant Pat. No. 5,262) and as female parent an unpatented undistributed seedling identified as 'FB-1'.

The resulting seedling of the new variety was grown and asexually propagated by runners(stolons) in Ferrara, Italy. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety. The varietal denomination of the new variety is 'Tethis.' Among the characteristics which distinguish the new variety from other varieties are a combination of traits which include a vigorous plant and large, firm fruit.

COMPARISON TO CLOSEST VARIETY

The new variety is closest to the variety 'Pajaro' (U.S. Plant Pat. No. 4,538), but is distinguished therefrom by the following characteristics.

1. The plant of the new variety has more vigorous growth with bigger leaves.

2. Leaves show more blistering than in 'Pajaro'.

3. Fruit of the new variety are bigger in size, with better flesh firmness. The fruit of the new variety have bi-conical shape, while the fruit of 'Pajaro' have cordate shape. The sepals of the fruit of the new variety are bigger than the sepals of 'Pajaro', and are reflexed.

The following Table 1 compares leaf characteristics of 'Pajaro' and 'Tethis' as determined in Battipaglia, Italy, in the month of April:

TABLE 1

| CHARACTER | 'Tethis' | 'Pajaro' |
|---|---|---|
| Leaf color (upper surface RHS) | 139A | 137A/B |
| Terminal leaflet mean length (cm) | 9.2 | 9.6 |
| Terminal Leaflet mean width (cm) | 9.1 | 8.3 |
| Terminal leaflet ratio (L/W) | 1.01 | 1.15 |
| Petiole mean length (cm) | 17.7 | 16.9 |

TABLE 1-continued

| CHARACTER | 'Tethis' | 'Pajaro' |
|---|---|---|
| Petiole mean width (mm) | 4.7 | 4.4 |
| Petiole pubescence | Medium-low | Medium |
| Petiole: pose of hairs | Upwards | Upwards |
| Petiole: color (RHS) | 141D | 141D |

The leaves of 'Tethis' are medium large in size, glossy and rugose. The terminal leaflet is as long as wide as described by the length/width ratio. Serrations at the margins are medium large, between 4.5 and 6 mm deep, normally single, seldom double, with moderately obtuse apexes. Petioles are long and medium large in diameter, with medium to low pubescence. Hairs grow upwards on the petiole. Stipules are in pairs and are green in color.

BRIEF DESCRIPTIONS OF ILLUSTRATIONS

The accompanying photographs show typical specimens of the new variety, including fruit, foliage and flower, in color as nearly true as it is reasonably possible to make in color illustrations of this character.

DESCRIPTION OF THE NEW VARIETY

Figure 1:
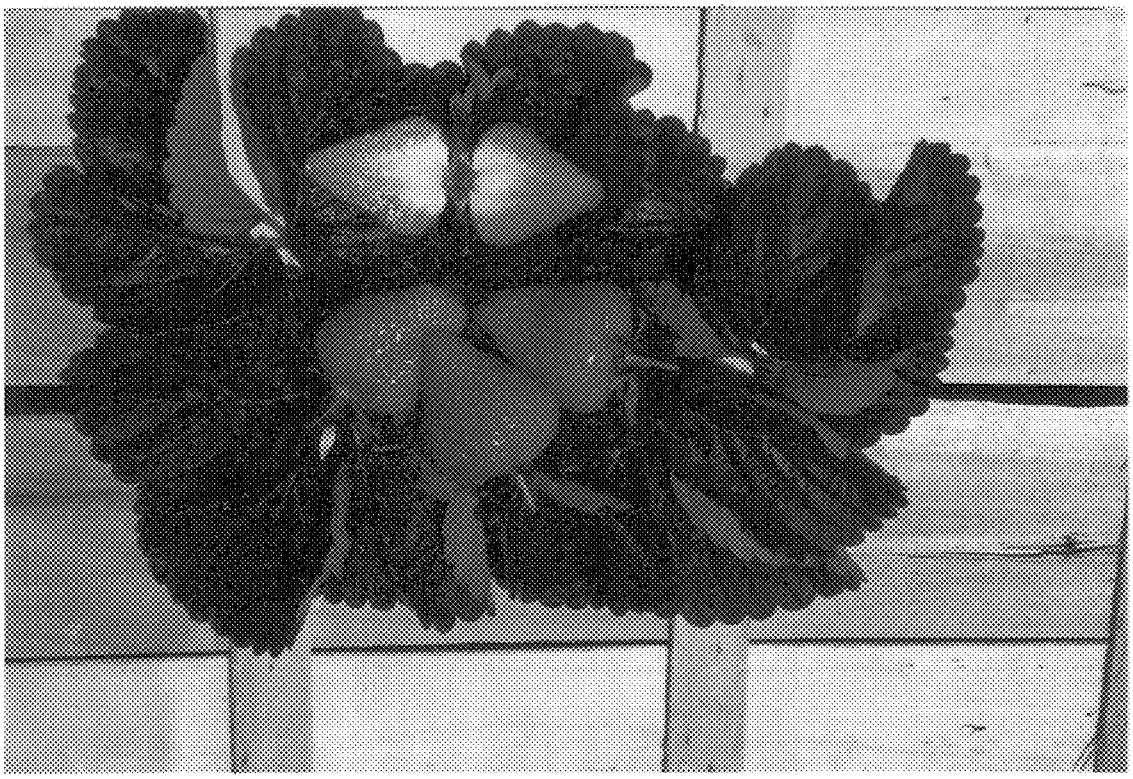
FIG. 1 shows typical fruit in cross section illustrating the typical flesh and flesh coloration, and conspicuous absent cavity, and whole fruit showing the bright red coloration.
Figure 2:
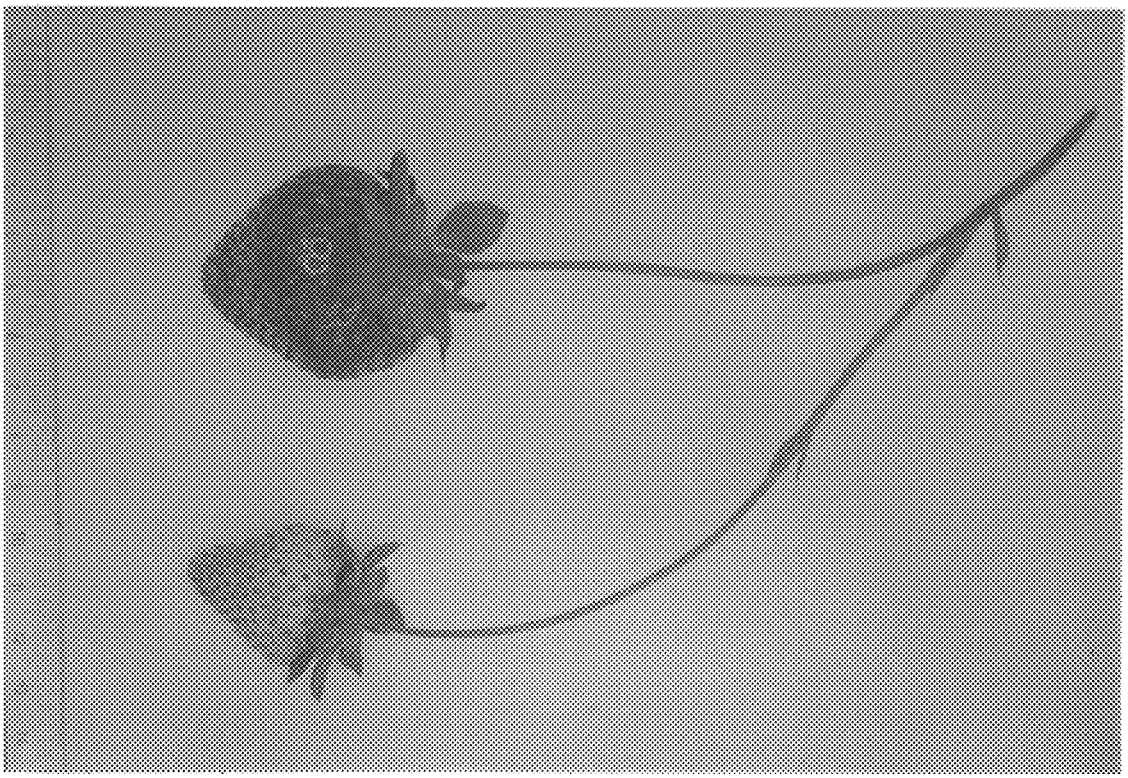
FIG. 2 shows a whole fruit and petiole.
Figure 3:
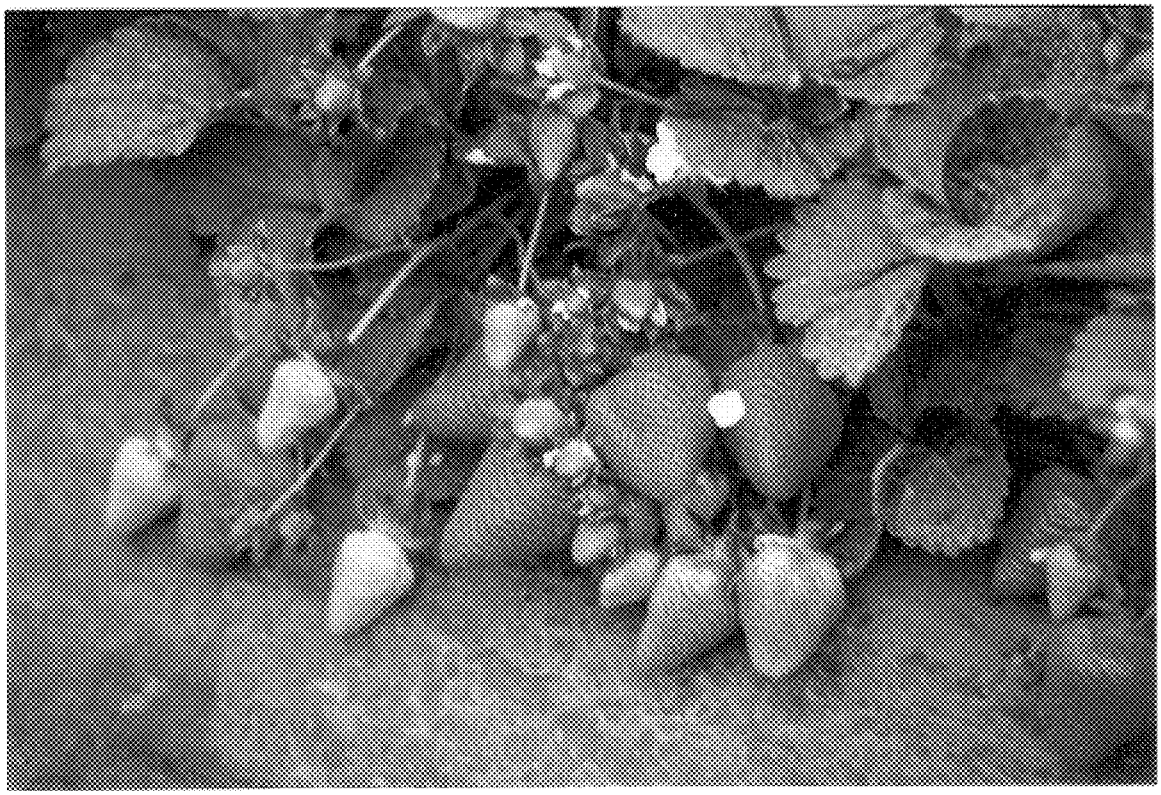
FIGS. 3, 4 and 5 show the fruit and foliage.
Figure 4:
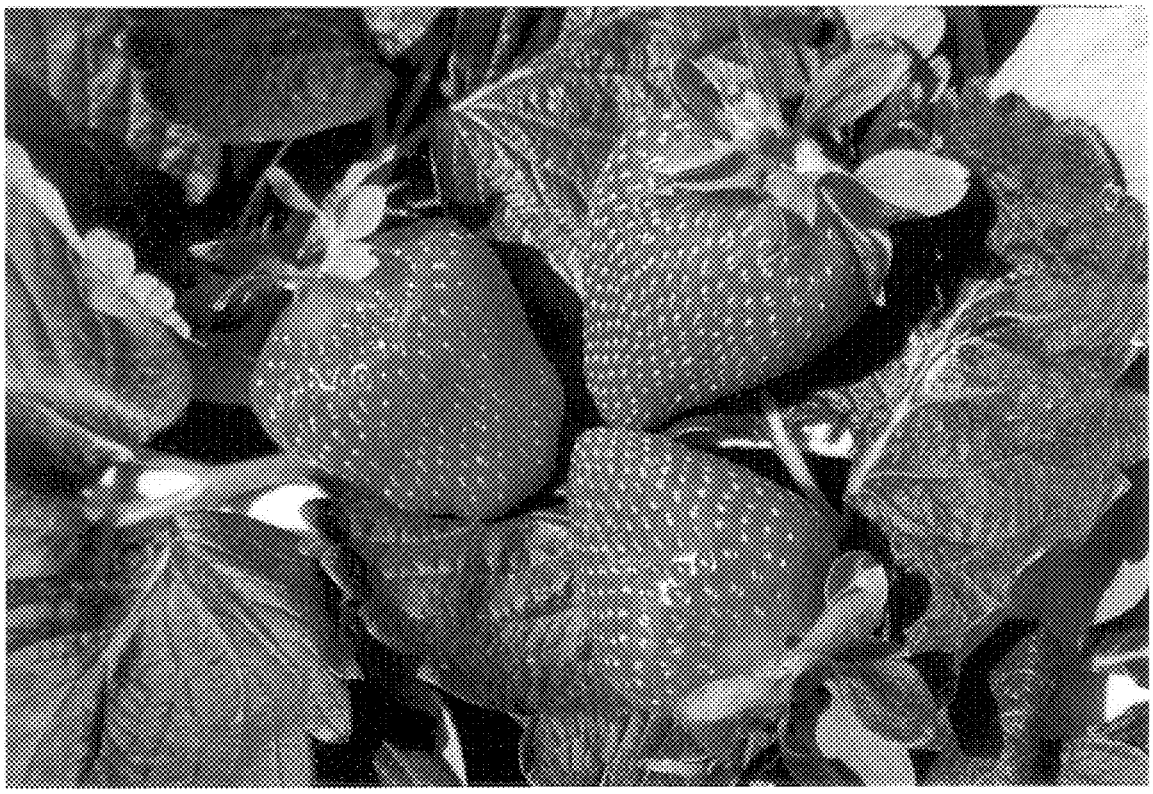
Figure 5:
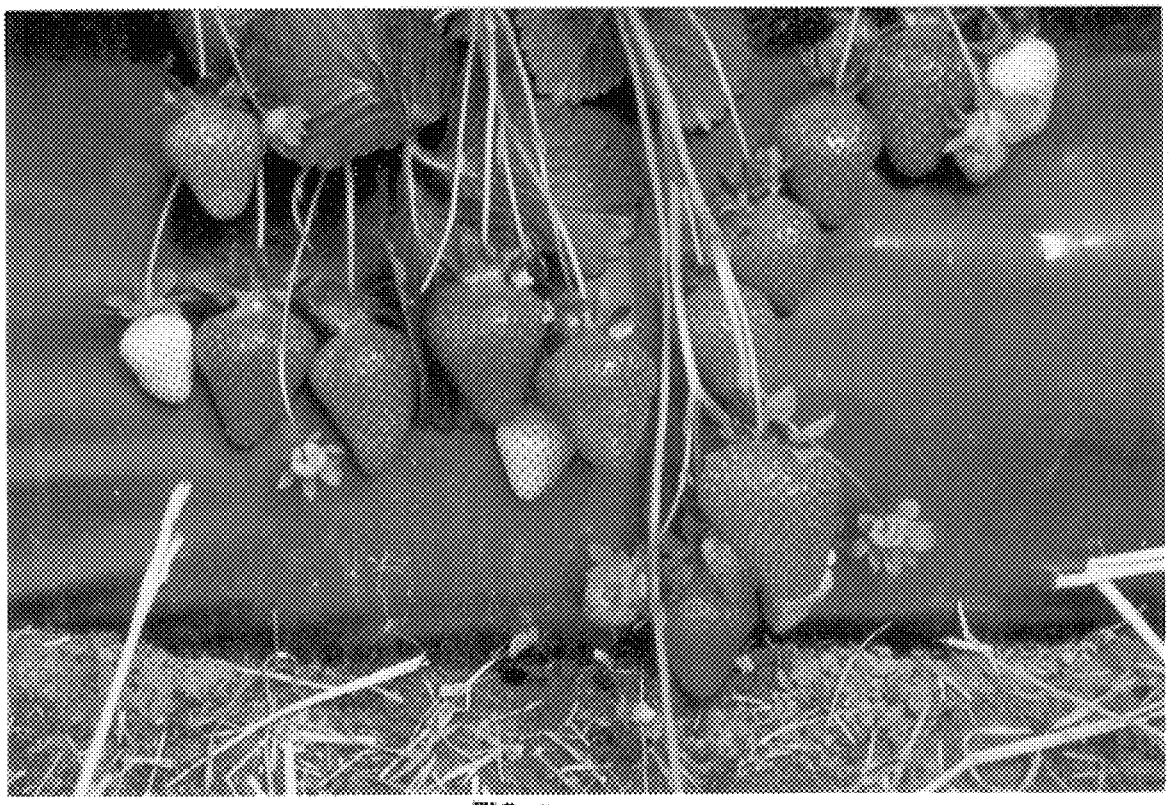
Figure 6:
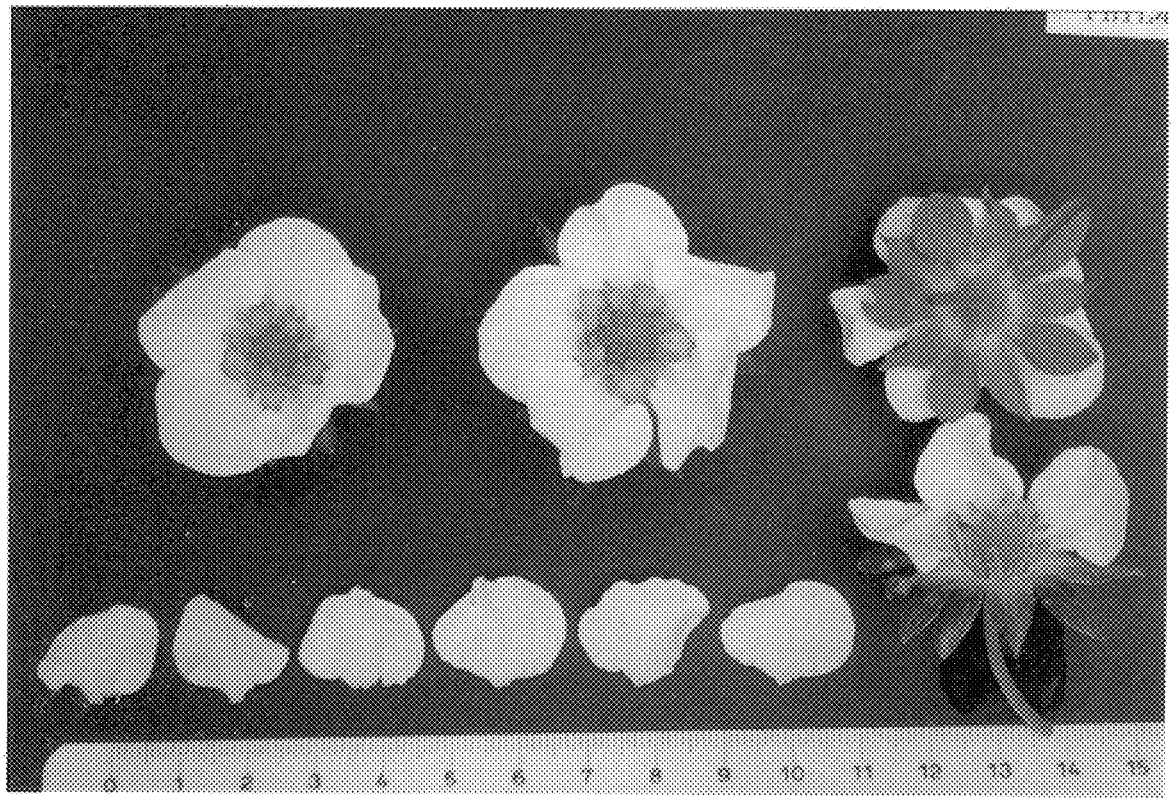
FIG. 6 shows the flower and reproductive organs of the new variety.
Figure 7:
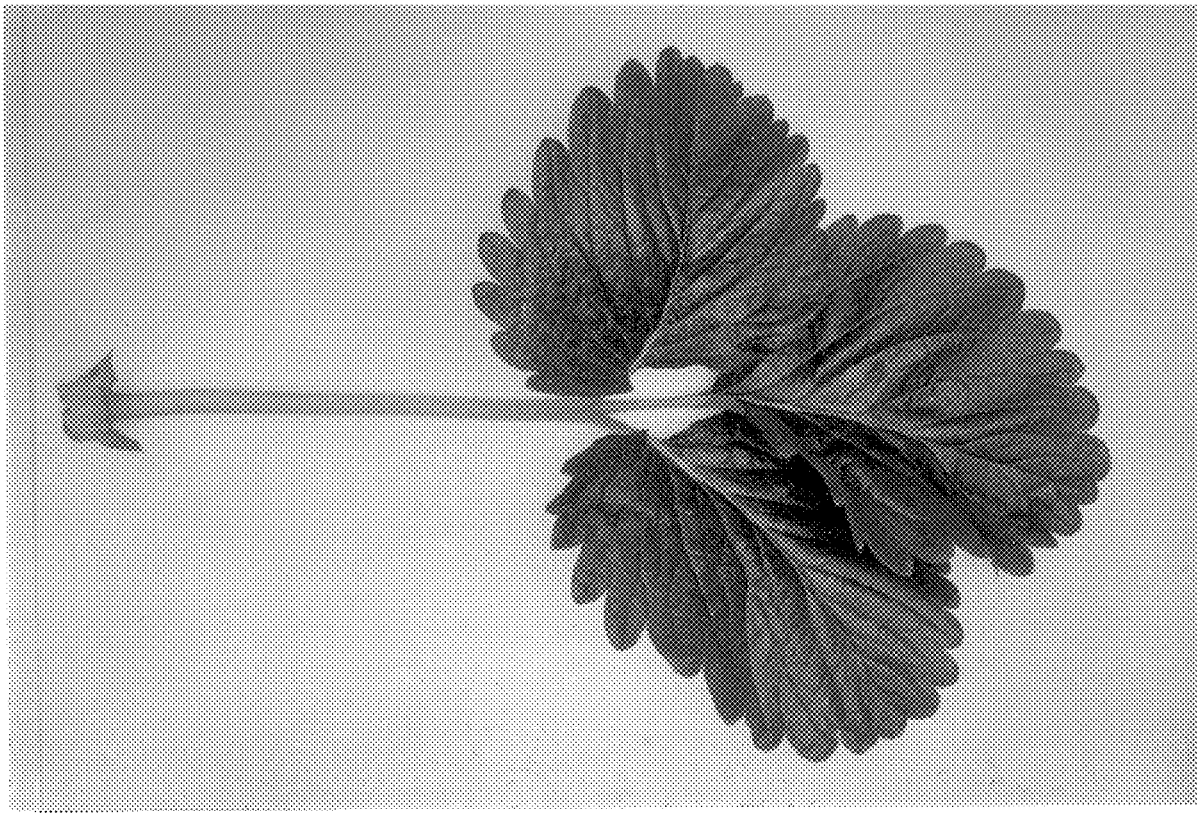
FIG. 7 shows the upper leaf surface of typical foliage of the new variety.

The following detailed description of the new variety is based upon observations taken of plants and fruits grown "underglass," in Naples, Italy, in the month of April.

The following description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

PROPAGATION

The new variety is principally propagated by way of runners (stolons). Although propagation by runners is presently preferred, other known methods of propagating strawberry plants, such as micropropagation, may be used. The new variety roots well after transplanting.

The term "blistering" used herein refers to the texture or rugosity inherent to leaves and is generally a constant characteristic.

PLANT

Size: About 23 to 30 cm.

Preferred plant time: September in Naples, Italy; peak production occurring in April (see above Table 1).

Leaves:

*Shape.*—As long as wide, shape of base obtuse.

*Color.*—Upper side near 139A; underside near 136C.

*Leaflet, number.*—3. Texture: Strong blistering. Serration: Obtuse.

*Growth habit.*—Erect.

*Regional or climatic growing preferences.*—Warm, with low chilling

*Peticoles, size and length.*—(See above Table 1).

*Runners.*—Vigorous, of medium quantity.

Inflorescence:

*Size and shape.*—Mean flower diameter about 34 mm (measured on plants grown in Battipaglia, Italy, in April).

*Inflorescence.*—Mean length about 24.2 cm, about 10–13 flower/inflorescence.

*Flowers.*—Normally about 5 petals/flower, petals are wider than long, ratio (L/W) about 0.8, color of petals in near 155D to 155C.

*Sepals.*—Normally about 10, calyx diameter about 28 mm.

*Peduncles.*—Upright hairs.

*Pedicel.*—Branching inflorescence, erect habit.

*Abundance.*—Abundant.

*Color.*—White, petals broader than long, overlapping.

*Anthers and pollen.*—Abundant pollen. Color: Yellow. Calyx size, sepal form and color: Big sepals, reflexed, inner calyx of same size as outer calyx.

Fruit:

*Size and shape.*—Large, prevalent shape, bi-conical, no significant differences between primary and secondary fruits (see Table 2 below).

*Seed characteristics.*—Inserted at the same level with surface, present on all the surface.

*Juiciness.*—Medium.

*Taste.*—Good balance between sugar and acid.

*Flesh color.*—Near 40B.

*Exterior surface.*—Color: Near 45A. Glossiness: Strong. Shape: Bi-conical. Firmness: Strong.

*Characteristics of flesh and core.*—Flesh is firm, medium red, medium cavity, good flavor.

*Aroma.*—Medium.

*Keeping qualities.*—Very good.

Disease resistance: Medium susceptibility to the principal strawberry root diseases and downy mildew.

Winter or frost resistance: Not suited for high chilling areas.

In the following Table 2 the mean yield of market fruit and fruit size of 'Tethis' are reported in comparison with 'Pajaro'; data based on observation of plants harvested from late March through first week of June in Battipaglia, Italy; production plants were cold stored plants planted in the first week of September of the year preceding the fruit harvest:

TABLE 2

| Mean 1996–97–98 | Market fruit yield g/plant | Fruit size grams |
|---|---|---|
| Tethis | 602 | 20.2 |
| Pajaro | 532 | 19.5 |

In the following Table 3 the fruit characteristics of 'Tethis' are reported in comparison with those of 'Pajaro'. The data are taken from plants harvested from late March through the first week of June 1998 in Battipaglia, Italy. The production plants were cold stored plants planted in the first week of September 1997.

TABLE 3

| 1998 | Soluble solids | Acidity | Flavor | Firmness |
|---|---|---|---|---|
| Tethis | 6.26 | 6.49 | 3.83 | 3.88 |
| Pajaro | 5.80 | 4.56 | 3.86 | 2.92 |

In the above Table 4 the soluble solids are expressed in Brix degrees, acidity in g/liter of citric acid, taste and firmness are rated 1 to 5, with 1 being the minimum and 5 being the maximum value. Five tests for each characteristic were repeated during the harvest season. The mean fruit width (measured across the widest part of the berry) is about 4.2 cm.; mean fruit length is about 5.3 cm; bud break takes place between January 20–30. The first bloom is mid February and lasts about 10 days as observed in Battipaglia, Italy.

The following table reports the beginning end of peak of harvest in 1997 in Battipaglia, Italy, in comparison with 'Pajaro'.

TABLE 4

| Harvest 1997 in Battipaglia | 'Tethis' | 'Pajaro' |
|---|---|---|
| Beginning | 28/March | 21/March |
| End | 06/June | 03/June |
| Peak | 18/April | 05/April |

The fruit of 'Tethis' were cooled to about 0° C. immediately after harvest and kept in cold storage for 2 days. Shelf life at room temperature after the treatment was about 4–5 days. These values are the results of the average of 5 trials during the harvest season in 1997.

We claim:

1. A new and distinct strawberry plant of the variety substantially as shown and described.

* * * * *